United States Patent
Cooper et al.

(10) Patent No.: US 10,376,331 B2
(45) Date of Patent: *Aug. 13, 2019

(54) SHEATHS FOR JOINTED INSTRUMENTS

(75) Inventors: Thomas G. Cooper, Menlo Park, CA (US); S. Christopher Anderson, San Francisco, CA (US); Matthew R. Williams, Walnut Creek, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 425 days.

This patent is subject to a terminal disclaimer.

(21) Appl. No.: 12/832,580

(22) Filed: Jul. 8, 2010

(65) Prior Publication Data

US 2012/0010628 A1   Jan. 12, 2012

Related U.S. Application Data (60) Provisional application No. 61/304,338, filed on Feb. 12, 2010.

(51) Int. Cl.
| | | |
|---|---|---|
| *A61B 18/14* | (2006.01) | |
| *A61B 18/00* | (2006.01) | |
| *A61B 34/30* | (2016.01) | |
| *A61B 90/00* | (2016.01) | |
| *A61B 46/13* | (2016.01) | |
| *A61B 34/35* | (2016.01) | |

(52) U.S. Cl.
CPC ............ *A61B 90/04* (2016.02); *A61B 34/30* (2016.02); *A61B 46/13* (2016.02); *A61B 18/1445* (2013.01); *A61B 2018/00083* (2013.01)

(58) Field of Classification Search
CPC ......... A61B 90/04; A61B 34/30; A61B 46/13; A61B 18/1445; A61B 2018/00083

USPC ............................................................ 606/1
See application file for complete search history.

(56) References Cited

U.S. PATENT DOCUMENTS

| | | | | |
|---|---|---|---|---|
| 3,953,566 | A | * 4/1976 | Gore ................ | B01D 71/36 264/127 |
| 3,962,153 | A | * 6/1976 | Gore ................ | B01D 67/0027 264/127 |
| 4,187,390 | A | * 2/1980 | Gore ................ | B01D 71/36 128/205.12 |
| 5,261,918 | A | * 11/1993 | Phillips et al. ... | 606/140 |

(Continued)

FOREIGN PATENT DOCUMENTS

| | | |
|---|---|---|
| EP | 1738705 A1 | 1/2007 |
| EP | 2042117 A1 | 4/2009 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

(Continued)

*Primary Examiner* — Boniface N Nganga
(74) *Attorney, Agent, or Firm* — Jones Robb, PLLC (57) ABSTRACT

Sheaths for medical instruments cover wrist mechanisms to provide a barrier to infiltration of biological material into the instrument, electrical isolation of energized portions of the instrument, seal the instrument to help maintain cavity pressure within a patient, or reduce the chance that two jointed instruments will tangle during a medical procedure.

20 Claims, 4 Drawing Sheets

(56) References Cited

U.S. PATENT DOCUMENTS

| | | | |
|---|---|---|---|
| 5,296,292 A * | 3/1994 | Butters | A01K 91/12 |
| | | | 428/373 |
| 5,415,157 A | 5/1995 | Welcome | |
| 5,417,203 A * | 5/1995 | Tovey et al. | 600/106 |
| 5,491,882 A | 2/1996 | Walston et al. | |
| 5,547,117 A | 8/1996 | Hamblin et al. | |
| 5,624,392 A | 4/1997 | Saab | |
| 5,724,994 A | 3/1998 | Simon et al. | |
| 6,004,509 A | 12/1999 | Dey et al. | |
| 6,016,848 A * | 1/2000 | Egres, Jr. | 138/137 |
| 6,091,993 A | 7/2000 | Bouchier et al. | |
| 6,099,537 A * | 8/2000 | Sugai | A61B 17/0684 |
| | | | 606/143 |
| 6,106,540 A | 8/2000 | White et al. | |
| 6,817,974 B2 * | 11/2004 | Cooper et al. | 600/142 |
| 6,994,708 B2 | 2/2006 | Manzo | |
| 7,320,700 B2 * | 1/2008 | Cooper et al. | 606/205 |
| 7,367,973 B2 | 5/2008 | Manzo et al. | |
| 7,785,252 B2 | 8/2010 | Danitz et al. | |
| 7,879,035 B2 | 2/2011 | Garrison et al. | |
| 9,089,351 B2 | 7/2015 | Park et al. | |
| 9,138,284 B2 | 9/2015 | Krom et al. | |
| 2002/0072712 A1 | 6/2002 | Nool et al. | |
| 2003/0125719 A1 | 7/2003 | Furnish | |
| 2003/0163128 A1 | 8/2003 | Patil et al. | |
| 2004/0098040 A1 * | 5/2004 | Taniguchi et al. | 606/205 |
| 2004/0122462 A1 | 6/2004 | Bakos et al. | |
| 2004/0230204 A1 * | 11/2004 | Wortley et al. | 606/108 |
| 2005/0216033 A1 | 9/2005 | Lee et al. | |
| 2006/0025654 A1 | 2/2006 | Suzuki et al. | |
| 2006/0079884 A1 * | 4/2006 | Manzo et al. | 606/41 |
| 2006/0079934 A1 | 4/2006 | Ogawa et al. | |
| 2006/0085054 A1 | 4/2006 | Zikorus et al. | |
| 2006/0247743 A1 | 11/2006 | Hayakawa et al. | |
| 2007/0005001 A1 * | 1/2007 | Rowe et al. | 604/19 |
| 2007/0027447 A1 | 2/2007 | Theroux et al. | |
| 2007/0112337 A1 | 5/2007 | Salman et al. | |
| 2007/0179486 A1 * | 8/2007 | Welch et al. | 606/15 |
| 2007/0239203 A1 | 10/2007 | Cooper et al. | |
| 2008/0046122 A1 | 2/2008 | Manzo et al. | |
| 2008/0188871 A1 | 8/2008 | Smith et al. | |
| 2008/0306335 A1 | 12/2008 | Lau et al. | |
| 2009/0082628 A1 * | 3/2009 | Kucklick et al. | 600/121 |
| 2009/0088738 A1 | 4/2009 | Guerra et al. | |
| 2009/0088741 A1 * | 4/2009 | Hushka | A61B 18/1445 |
| | | | 606/41 |
| 2009/0088747 A1 * | 4/2009 | Hushka et al. | 606/51 |
| 2009/0177141 A1 * | 7/2009 | Kucklick | 604/35 |
| 2009/0182201 A1 * | 7/2009 | Kucklick et al. | 600/156 |
| 2009/0254162 A1 | 10/2009 | Quinci et al. | |
| 2009/0287194 A1 | 11/2009 | Gertz et al. | |
| 2010/0016852 A1 | 1/2010 | Manzo et al. | |
| 2010/0168510 A1 * | 7/2010 | Rogers et al. | 600/104 |
| 2010/0268163 A1 * | 10/2010 | Rowe et al. | 604/167.03 |
| 2011/0087070 A1 * | 4/2011 | Tilson | A61B 1/00135 |
| | | | 600/121 |
| 2012/0010611 A1 | 1/2012 | Krom et al. | |
| 2012/0065472 A1 | 3/2012 | Doyle et al. | |
| 2012/0065645 A1 | 3/2012 | Doyle et al. | |
| 2013/0123805 A1 | 5/2013 | Park et al. | |
| 2014/0171943 A1 | 6/2014 | Weitzner et al. | |
| 2015/0313678 A1 | 11/2015 | Park et al. | |
| 2015/0359587 A1 | 12/2015 | Krom et al. | |

FOREIGN PATENT DOCUMENTS

| | | |
|---|---|---|
| JP | 2010075565 A | 4/2010 |
| WO | WO 2005032642 A2 * | 4/2005 |

OTHER PUBLICATIONS

PCT/US2011/041842 International Search Report and Written Opinion of the International Searching Authority, dated Oct. 31, 2011, 10 pages.

Wigner et al., "Use of Expanded PTFE Membranes in Medical Filtration," https://www.mdtmag.com/article/2009/08/use-expanded-ptfe-membranes-medical-filtration, Aug. 28, 2009, 10 pages.

* cited by examiner

SHEATHS FOR JOINTED INSTRUMENTS

CROSS-REFERENCE TO RELATED APPLICATIONS

This patent document claims benefit of the earlier filing date of U.S. Pat. App. No. 61/304,338, filed Feb. 12, 2010, which is hereby incorporated by reference in its entirety.

BACKGROUND

Robotically controlled surgical instruments are often used in minimally invasive medical procedures. (As used herein, the terms "robot" or "robotically" and the like include teleoperation or telerobotic aspects.) Such instruments typically includes an end effector or tool such as forceps, a cutting tool, or a cauterizing tool mounted on a wrist mechanism at the distal end of an extension, sometimes referred to herein as the main tube of the instrument. During a medical procedure, the effector and the distal end of the main tube can be inserted directly or through a cannula into a small incision or a natural orifice of a patient to position the effector at a work site within the body of the patient. The wrist mechanism can then be used to position, orient, move, and operate the effector when performing the desired procedure at the work site. Tendons, e.g., cables or similar structures, extending through the main tube of the instrument can connect the wrist mechanism to a transmission or backend mechanism that may be motor driven in response to a doctor's instructions provided through a computer interface.

The instruments employed during medical procedures are generally complex mechanical devices having many separate components (e.g., cables and mechanical members.) Accordingly, to reduce cost, it is desirable for the instruments to be reusable. However, reuse of a medical instrument generally requires stringent cleaning and sterilization procedures that are made more difficult by the large number of small components and tight intervening spaces within such instruments. Systems and methods for improving the efficiency of cleaning procedures for minimally invasive medical instruments and/or reducing the cost per use of such instruments are desired.

SUMMARY

In accordance with an aspect of the invention, a medical apparatus includes a removable sheath having a body with a section positioned to surround a joint of an instrument when the sheath is installed on the instrument, and the section surrounding the joint has convolutions that accommodate bending of the joint.

In accordance with another aspect of the invention, a medical apparatus includes a removable sheath having a body with a tubular section of a flexible material positioned to surround a joint of a medical instrument when the sheath is installed on the medical instrument. The sheath also includes a support structure such as a coil spring that is arranged to prevent collapse of the tubular section when the joint bends.

In accordance with yet another aspect of the invention, a medical apparatus includes a removable sheath having a body with a section of porous material such as expanded PTFE. The section of porous material is positioned to surround a joint of the medical instrument and provide a barrier to infiltration of liquids into the instrument. The porous material has a pore structure that prevents collapse of the section during bending of the joint.

In accordance with still another aspect of the invention, a medical apparatus including a removable sheath for a jointed medical instrument can employ a retaining structure of a resilient material that is shaped to engage a complementary feature on the medical instrument and removeably lock the sheath in an installed position on the instrument.

In accordance with still another aspect of the invention, a medical apparatus including a removable sheath can include an agent in the interior of the sheath, wherein the agent is a lubricant for the instrument, a disinfectant, or an agent that assists in cleaning of the instrument on which the sheath can be installed.

BRIEF DESCRIPTION OF THE DRAWINGS

Use of the same reference symbols in different figures indicates similar or identical items.

DETAILED DESCRIPTION

In accordance with an aspect of the invention, a medical instrument for robotic minimally invasive procedures employs a replaceable sheath to cover a wrist mechanism or other joints in the instrument. The instrument and the sheath can employ cooperative seal and retaining structures that keep the sheath in place on the instrument, seal the instrument from infiltration of biological material, and provide an opening for an end effector of the instrument to operate without obstruction. The replaceable sheath can provide a variety of functions including: reducing or preventing infiltration of biomaterial into the instrument during a medical procedure; providing electrical isolation of at least a portion of the medical instrument; sealing the instrument to assist in maintaining an elevated pressure at the work site within a patient; providing smooth surface that facilitates insertion of the instrument through a cannula, and reducing the chance that a wrist mechanism of one instrument will catch on or tangle another instrument or other components of a robotic medical system or other complex medical system.

Bending at a joint in a robotic medical instrument typically causes a large difference between lengths of portions of a sheath at the inside and outside of the curve created at the joint, often resulting in strains on the order of 30 to 50% in a sheath. Many potential sheath materials that have desirable electrical characteristics are not sufficiently stretchy or flexible enough to withstand the strain at a bending joint. For example, materials such as polyester and fluoropolymers such as polytetrafluoroethylene (PTFE), ethylene tetrafluoroethylene (ETFE), fluorinated ethylene-propylene FEP, and perfluoroalkoxy polymer resin (PFA) have relatively high dielectric strength but may not provide sufficient stretch or flexibility to withstand the bending at a mechanical joint. In accordance with an aspect of the invention, such materials can be contoured (e.g., corrugated or convoluted) at locations corresponding to mechanical joints to accommodate length differences between the inside and outside of a bend. Alternatively, a sheath can be made of expanded or porous material (e.g., expanded PTFE) that provides a barrier to liquids and electrical current and also has a pore structure that allows the material to withstand the strain at a bend.

The material and construction of particular embodiments of the sheaths described herein can be flexible at a wrist mechanism or other mechanical joints of the instrument so that a sheath by itself can provide a fluid or electrical barrier and the desired range of motion of the instrument without becoming caught in the covered mechanisms during instrument operation. Accordingly, the sheaths can be used with jointed instruments without being damaged by instrument movement or interfering with the instrument operation.

In accordance with a further aspect of the invention, removable sheaths employed can contain or be internally coated with an agent such as a lubricant, a disinfectant, or an anticoagulant that lubricates mechanism of the instrument or facilitates cleaning of the instrument.

Figure 1:
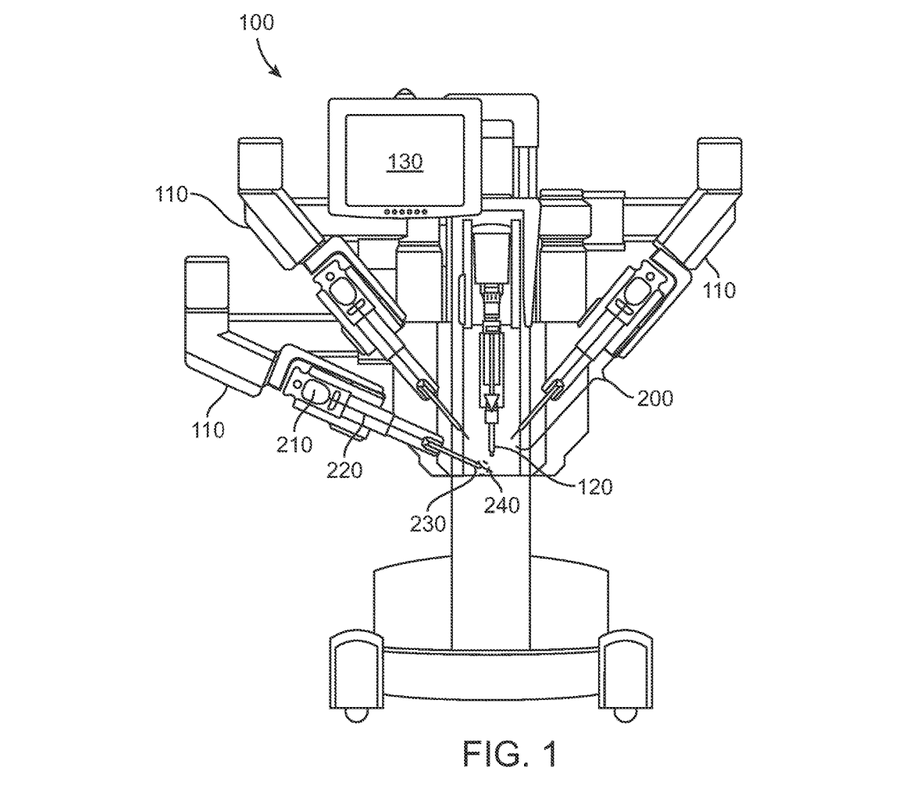
FIG. 1 shows a system having multiple arms on which instruments for minimally invasive medical procedures can be attached.

FIG. 1 shows an example of a robotically controlled system 100 that can employ sheathed instruments in accordance with an embodiment of the invention. System 100, which may, for example, be a da Vinci® Surgical System available from Intuitive Surgical, Inc. includes multiple medical instruments 200, each of which is mounted in a docking port on a robotic arm 110. Instruments 200 can be interchangeable, so that the instruments 200 mounted on arms 110 can be selected for a particular medical procedure or changed during a medical procedure to provide the clinical functions needed. As is well known in the art, instruments 200 can implement many functions including but not limited to forceps or graspers, needle drivers, scalpels, scissors, and cauterizing tools.

The docking ports of system 100 generally include drive motors that provide mechanical power for operation of instruments 200. The docking ports may additionally include an electrical interface for communication with instruments 200, for example, to identify the type of instrument in the docking port, to access parameters of the instrument, or convey measurements obtained using the instruments. High voltage electrical systems (not shown) such as generators for cauterizing or sealing instruments would typically connect to suitable instruments 200 through separate connectors but could alternatively be provided through built-in circuits in control system 100.

Each instrument 200 generally includes a transmission or backend mechanism 210, a main tube 220 extending from the backend mechanism 210, a wrist mechanism 230 at the distal end of main tube 220, and an end effector 240 extending from wrist mechanism 230. Drive cables or tendons and electrical conductors that are connected to wrist mechanism 200 in an instrument 200 may extend through main tube 220 and connect to backend mechanism 210. Backend mechanism 210 typically provides a mechanical coupling of the drive tendons to drive motors in control system 100. System 100 can thus control movement and tension in the tendons as needed to move or position wrist mechanism 230 and operate effector 240. A camera system 120 can similarly be mounted on an arm of system 100 and have a wrist mechanism that system 100 operates to position a distal end of camera system 120 for viewing of a work site and the operation of instruments 200 within a patient. The views from camera system 120, which may be stereoscopic or three-dimensional, can be viewed at a control console (not shown) and images may be displayed on a monitor 130. A processing system of system 100 can thus provide a user interface enabling a doctor or other medical personnel to see and manipulate the camera system 120 and instruments 200. For example, an arm 110 can be used to insert the end of a medical instrument 200 through a cannula in small incisions in a patient undergoing a medical procedure and to operate wrist mechanism 230 and effector 240 at a worksite inside the patient. The diameter or diameters of main tube 220, wrist mechanism 230, and effector 240 are generally selected according to the size of the cannula with which the instrument will be used, and in an exemplary embodiment, wrist mechanism 200 and main tube 110 are about 4 mm, 5 mm, or 8 mm in diameter to match the sizes of some existing cannula systems.

Main tube 220 may contain both drive tendons and electrical conductors that run from backend mechanism 210 to wrist mechanism 230 and effector 240. In general, main tube 220 may be rigid or flexible. A flexible main tube 220 would be used, for example, for insertion through an endoscope or other guide or cannula that follows a natural lumen or otherwise curved path. However, many common types of minimally invasive medical procedures such as laparoscopic surgery employ straight cannulas for insertion and removal of instruments, permitting use of a rigid main tube 220. A rigid main tube 220 can provide a more solid base for use of wrist mechanism 230 and effector 240 during a medical procedure. A rigid and straight main tube 220 also permits portions of drive tendons extending through main tube 110 to be structures such as rods or tubes (e.g., hypotubes) that may provide better immunity to stretching or be less expensive. Whether flexible or rigid, main tube 220 would generally experience minimal movement during operation of wrist mechanism 230.

Figure 2:
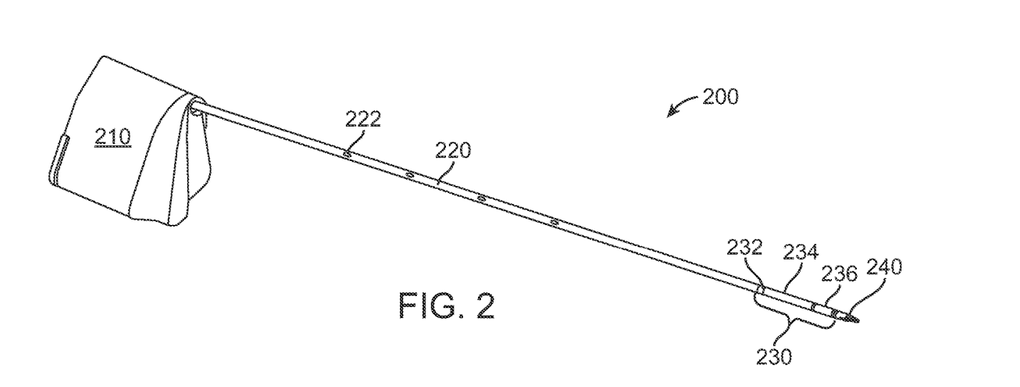
FIG. 2 shows an instrument that may be employed in the system of FIG. 1 and use replaceable sheaths in accordance with an embodiment of the invention.

FIG. 2 shows a medical instrument 200 in more detail and particularly illustrates one specific embodiment of a wrist mechanism 230 and effector 240, which are the components of medical instrument 200 that generally move extensively during a medical procedure. In the illustrated embodiment, wrist mechanism 230 includes a joint 232 that connects an extended member 234 to main tube 220, and extended member 234 connects to a multi-member wrist 236 on which effector 240 is mounted. Joint 232 can have two angular degrees of freedom for movement of member 234, which, as a result of the extended length of member 234, provides a significant range of spatial motion for wrist 236 and effector 240. Wrist 236 includes multiple vertebrae that may be independently controlled to provide multiple degrees of freedom for moving and orienting effector 240 during a medical procedure. The specifics of wrist mechanism 230 are provided here as merely as an illustration of one type of wrist mechanism. Many other types of wrist mechanisms are known and could be used with removable sheaths as described herein. For example, U.S. Pat. No. 6,817,974, entitled "Surgical tool having Positively Positionable Tendon-Actuated Multi-Disk Wrist Joint," to Cooper et al. describes some known wrist mechanisms containing multiple disks and tendon controlled joints. Of importance for the present invention is that, wrist mechanisms in the medical instruments commonly have joints with significant ranges (e.g., up to 30° or 40° from straight for a single joint), and each joint may be repeatedly exercised during typical medical procedures. Such joints make provision of sheathing complex because overly compliant sheathing can interfere with joint motion, be pinched during joint motion, or wear through as the result of repeated motion, and stiff sheathing may restrict joint motion or tear.

FIG. 2 also illustrates that main tube 220 may include a series of cleaning holes 222, which facilitate cleaning of the interior of instrument 200 between medical procedures. Conventionally, such cleaning holes have the drawback of creating flow paths for biological material or gas flow from a region of elevated pressure that may be maintained in a patient during a medical procedure. However, in accordance with an aspect of the current invention, a replaceable sheath can be installed on instrument 200 and seal cleaning holes 222 to help maintain a pressure differential during a medical procedure. Further, the sheath can be removed between medical procedures to permit access to cleaning holes 220 when instrument 200 is cleaned. Cleaning holes (not shown) can also be in wrist mechanism 230, for example, in extended member 234. The sheath can also seal wrist mechanism 230 but in case of contamination, can be removed to permit cleaning of an instrument protected by the sheath. On a camera instrument, which may be relatively large or have lower mechanical load requirements, the cleaning holes can be made large to enable easy cleaning, while the sheath reduces the amount of access that biomaterial has to the camera system during use. Instruments such as camera systems that are not generally in direct contact with biomaterial may not require a full seal.

Figure 3A:
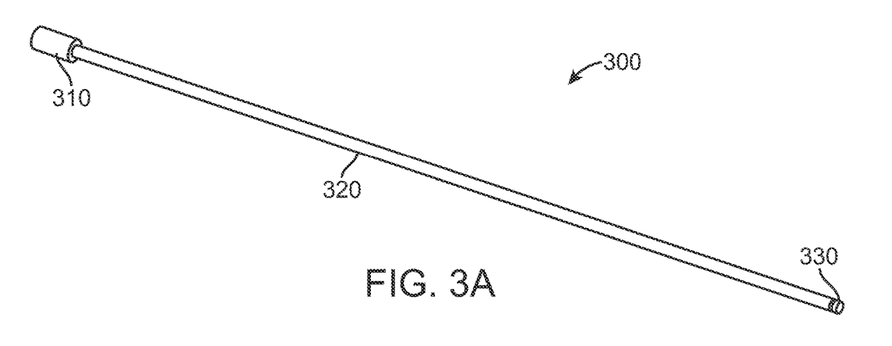
FIG. 3A shows a sheath in accordance with an embodiment of the invention having flexible pressure fit end seals.

FIG. 3A shows a sheath 300 in accordance with an embodiment of the invention that can be used with a jointed medical instrument. (Medical instrument is used here in a broad sense to include instruments 200 with end effectors and camera systems 120 such as described above with reference to FIGS. 1 and 2 and any similar components of a medical apparatus that may be employed in a minimally invasive medical procedure.) Sheath 300 includes a first end piece or base 310, a tube or generally tubular body 320, and a second end piece or tip 330. Sheath 300 has an inner diameter sized to accommodate the main tube 220 of a medical instrument (e.g., typically 4 mm to 8 mm), and tube 310 and tip 330 may have an outer diameter sized to fit within a cannula, which may be employed to guide the instrument.

Body 320 generally provides a flexible abrasion resistant surface that can act as a barrier to fluids and/or electricity. In an exemplary embodiment, body 320 is made of a relatively rigid material that resists kinking, buckling, or cracking. For example, body 320 may be a tube of a polyester such as Mylar, a fluoropolymer such as PTFE, ETFE, FEP, and PFA, a polyimide such as Kapton, or a multi-ply construction including different materials such as Mylar, Kapton, urethane, silicon or a woven fiber such as a para-aramid synthetic fiber (e.g., Kevlar®.) Tube 320 would typically have a circular cross-section but may have any cross-section need to match a medical instrument or camera system being sheathed. A typical sheath may have one or more layers with a typical thickness of about 0.003" depending on requirements for the strength, flexibility, and electrical insulating properties of the sheath. In one specific embodiment, tube 320 can employ heat shrinkable polyester tubing, which is commercially available from suppliers such as Advanced Polymers, Inc. However, with a multi-ply construction, the different materials can be chosen to add different overall characteristics to the sheath. For example, Kapton and Mylar would provide good dielectric properties while a para-aramid fiber would provide structural stability. As described further below, a high degree of elasticity or accommodation of bending is not required for most of body 320, so that the composition of the portions of body 320 that do not bend can be selected for other desirable characteristics such as a high dielectric constant when electrical isolation is desired.

End pieces 310 and 330 seal against a medical instrument as described further below. End pieces 310 and 330 may be predominantly made of a flexible material such as silicone or urethane that is molded over and/or bonded to opposite ends of body 320. End piece 310 or 330 may further include a more resilient portion that is shaped to removeably lock into a complementary feature on a medical instrument to keep sheath 300 in an installed position until sheath 300 is removed for instrument cleaning.

Figure 3B:
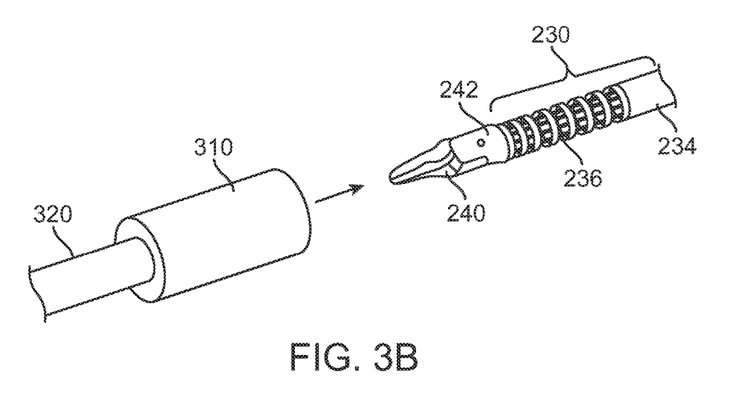
FIG. 3B illustrates installation of the sheath of FIG. 3A onto the instrument of FIG. 2.

Sheath 300 can be installed on an instrument 200 by sliding sheath 300 over the effector 240, wrist mechanism 230, and main tube 220 as illustrated in FIG. 3B. In an exemplary embodiment, a large section of sheath body 320 is relatively rigid and holds its shape during and after installation. Preferably, the material or composition of one section of body 320 is sufficiently rigid to avoid buckling during installation or as a result of friction with a cannula during medical procedures when a cannula guides an instrument having a sheath 300 installed.

Figure 3C:
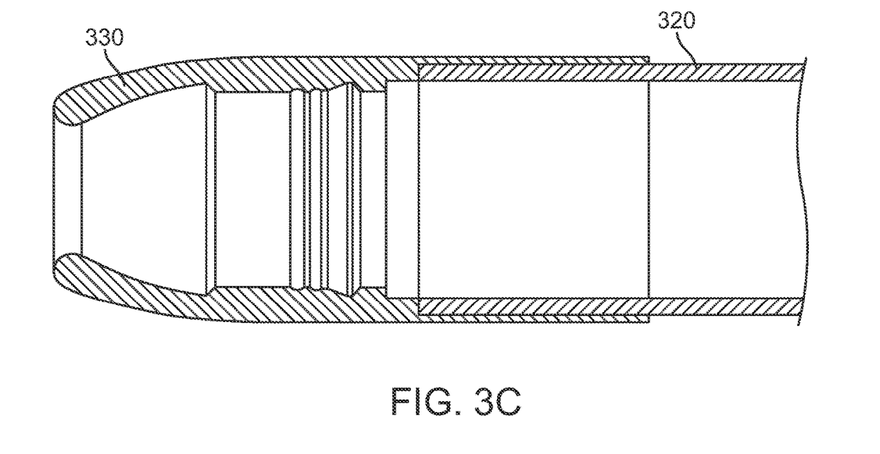
FIG. 3C illustrates a portion of a sheath in accordance with an embodiment of the invention having an end piece with an interior shaped to fit against the mechanism of a medical instrument.
Figure 3D:
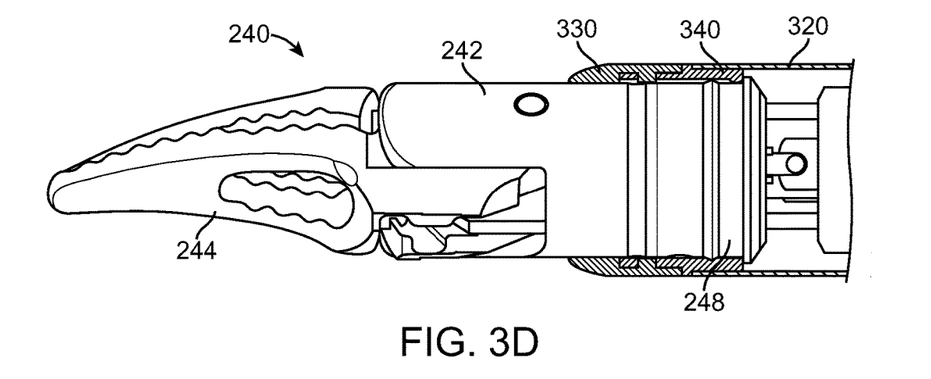
FIG. 3D is a partial cutaway view showing details of a distal seal and retaining structure in accordance with an embodiment of the invention.

End pieces 310 and 330, which may be bonded to body 320, contain an elastic material and stretch over the instrument during installation of sheath 300. The elastic material in ends 310 and 320 can provide friction seals against respective surfaces of effector 230 and main tube 220. FIG. 3C, for example, illustrates an embodiment of sheath 300 in which tip 330 has an interior shaped to match the outer surface of the portion of the medical instrument (e.g., a portion of the end effector 240), so that tip 330 tends to fit into and remain in a desired position on the instrument. As shown in FIG. 3D, elastic tension in tip 330 can cause tip 330 to seal against a base member 242 of effector 240. Effector 240, as shown, extends through a hole in tip 330 so that working portions (e.g., scissors or forceps jaws 244) of effector 240 are unobstructed when sheath 300 is installed. Optionally, separate seals (not shown) can be provided for tendons or other structures that may extend through base member 342 for operation of effector 240.

FIG. 3D also illustrates that sheath 300 may additionally include a retaining structure 340 such as a snap. For example, retaining structure 340 can be made of a resilient material such as a plastic (e.g., ultem) that flexes away from instrument 200 during installation of sheath 300 and snaps into a complementary groove 248 in base member 242 when sheath 300 reaches a fully installed position. Alternatively, retaining structure 340 could include a female thread pattern that engages a complement thread pattern on base member 242 or elsewhere on instrument 200. Structure 340 when engaged with instrument 200 resists further movement of sheath 300 during installation and use of instrument 200, while being easily removed by hand or with a suitable removal tool.

Figure 3E:
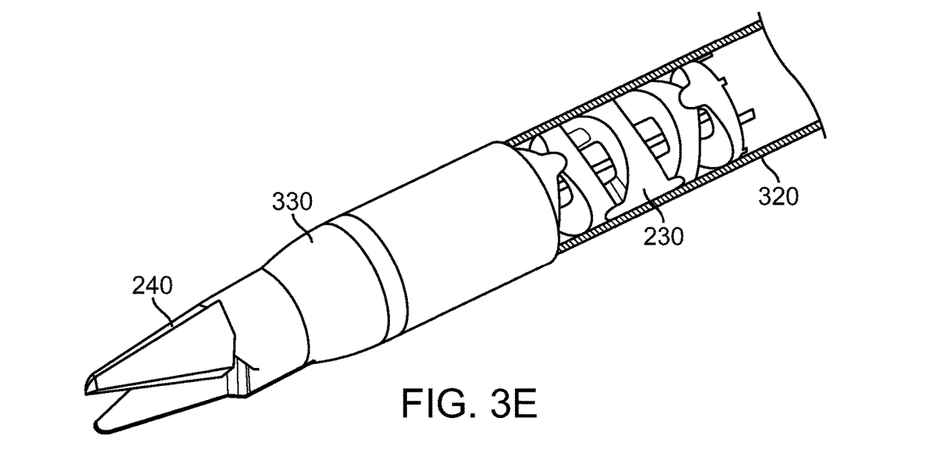
FIG. 3E shows a partial cutaway view of the distal end of an instrument with a removable sheath in accordance with an embodiment of the invention installed.

FIG. 3E shows tip 330 in the fully installed position with an end effector 240 extending outward from tip 330. However, wrist joints 230 are surrounded by a section of body 320 that provides the flexibility to accommodate bending of joints 230 without being damaged or interfering with the movement of joints 230. As described further below, this may be achieved in that section of body 320 by providing convolutions in body 320, employing a material with suitable pore structure, or employing a flexible material with an integrated support structure.

Figure 3F:
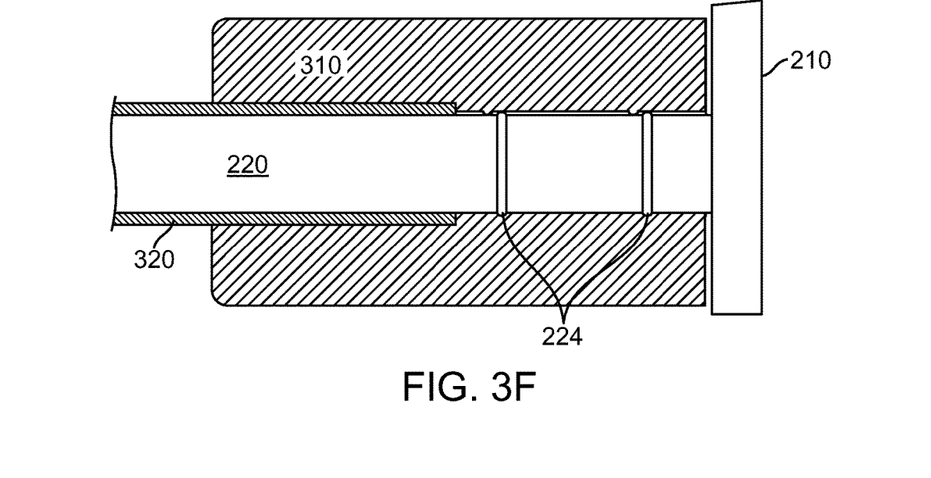
FIG. 3F is a partial cutaway view showing details of a proximal end of an instrument with a removable sheath in accordance with an embodiment of the invention installed.

End piece or base 310 similarly seals sheath 300 when installed on an instrument. In one embodiment of the invention, base 310 is at or near backend mechanism 210 of instrument 200 when sheath 300 is fully installed. FIG. 3F, for example, illustrates a configuration where base 310 is adjacent to backend mechanism 210 and provides a friction seal against main tube 220. With this configuration, sheath 300 can seal and or electrically isolate nearly the entire length of main tube 220. FIG. 3F also illustrates that main tube 220 may optionally have ridges 224 or other features shaped to engage base 310 to provide a more secure seal or better resist slipping of sheath 300 during a medical procedure. Base 310 may further include a retaining structure (not shown) made of a resilient material that engages a complementary feature of main tube 220 to releaseably lock the proximal end of sheath 300 in place.

Figure 4A:
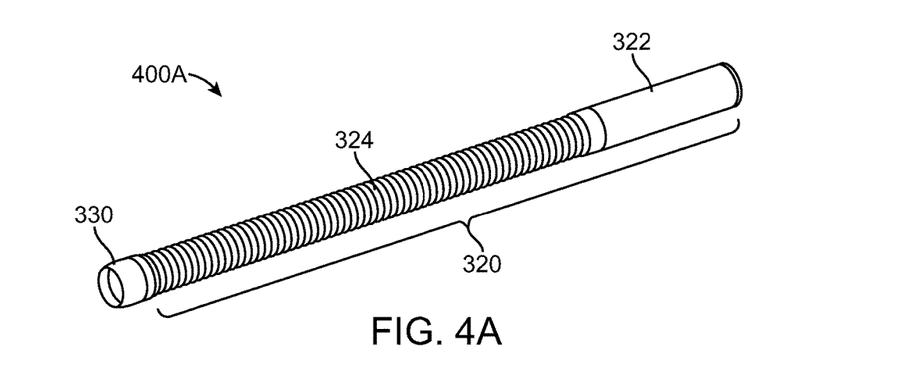
FIG. 4A illustrates a portion of a sheath in accordance with an embodiment of the invention using corrugations to improve flexibility where the sheath covers a wrist mechanism.

Sheath 300, as described above, can cover a wrist mechanism 230 when installed on a medical instrument 200. In accordance with an aspect of the invention, the section of body 320 that is positioned to surround wrist mechanism 230 (or other joints in a medical instrument) is fabricated to provide the necessary flexibility for movement of the wrist mechanism without being caught in the wrist mechanism or otherwise becoming damaged or interfering with movement of the medical instrument. Further, the force required to bend sheath 300 at the joints should also be small, so that sheath 300 does not interfere with the range of motion of the instrument or the therapeutic forces that the instrument can deliver when used in a robotic medical apparatus. FIG. 4A illustrates an embodiment of the invention in which body 320 includes two tubular sections 322 and 324 that can be made of the same basic material or composition but are shaped to create different flexibilities. In particular, section 324 is corrugated or convoluted in a manner that allows section 324 to bend without kinking or collapsing and allows section 324 to be repeatedly bent without creating stress fractures or fatigue fractures.

Convolutions in section 324 can be made, for example, by heat shrinking a material such as polyester that is wrapped around a spring held at fixed length while the polyester is also held at a fixed length. The first heating will thus form convolutions with a spacing defined by coils of the spring. The material can then be further shrunk with the spring free to contract, or even with the spring under axial compression, to increase the depth of the convolutions and increase flexibility. The spring used in the fabrication of section 324 can be left in sheath 300 as a support structure or removed.

The required length and position of section 324 in general will depend on the location of the joints in the instrument to be sheathed. In the example of FIG. 4A, section 324 is at the distal end of sheath 300, which corresponds to the locations of wrist mechanism 230 including multi-member or snake joint 232, extended member 234, and joint 236 in instrument 200 (FIG. 2). If additional mechanical joints were present along the instrument to be sheathed, the length of section 324 could be extended to cover other joints, or body 320 could include multiple separated, corrugated or convoluted sections for the separated mechanical joints. Covering joints in this manner can be advantageous when an instrument is inserted through a cannula because sheath 320 can prevent mechanical links within the joints from snagging on features of the cannula such as a trapdoor or seals. Section 322 of body 320 is preferably more rigid than section 324 to better resist buckling and provide a smoother structure for installation on an instrument, insertion through a cannula, and sealing on a cannula seal. The greater rigidity of section 322 can be inherent to the straight rather than convoluted topography of section 322, or section 322 may additionally be made thicker than section 324, have thicker layers than does section 324, or have a different composition from section 322. In general, the maximum permitted outer diameters of both sections 322 and 324 are limited by the cannula used with an instrument on which sheath 300 is installed, so that the lack of convolutions in section 322 permits use of thicker material in section 322.

Sheath 300 can employ other or additional techniques or structures to alter the stiffness of different sections of body 320. For example, body 320 can include multiple layers of different materials such as a Mylar layer surrounded by structural fiber (e.g., a woven or braided aramid fiber) then another layer of Mylar. Walls in one or more sections of body 320 could then have different thicknesses for one or more of the layers to modify the relative stiffness of a section (e.g., section 324) that surrounds an instrument joint when compared to a section (e.g., section 324) of body 320 that surrounds a rigid member or portion of the main tube of the instrument. For example, section 322 could have an outer layer of Mylar about 0.006" thick, a layer of fiber about 0.003" thick, and an inner layer of Mylar about 0.003 to make a stiff tube, while section 324 has an outer layer of Mylar about 0.002" thick, reinforcing fiber about 0.003" thick, and the inner layer of Mylar about 0.002" thick. The different sections could also be formed over a spring or corrugated mandrel that form convolutions in section 324 to assist with the flexibility of the multilayer sheath.

In accordance with yet another embodiment of the invention, a one-piece sheath made of a stretchy material such as silicone or urethane, which has a tendency to collapse when a joint bends, can be re-enforced with an integrated spring or other structure that allows the material to better retain its cross-sectional shape or diameter when bent. For example, a sheath made of silicone tube can contain a coil spring extending either along the length of body 320 or the section 324 of sheath 300 that is intended to cover one or more joints of an instrument. Use of a flexible or stretch material allows integration of end pieces 310 and 330 in a single molded structure with body 320.

Figure 4B:
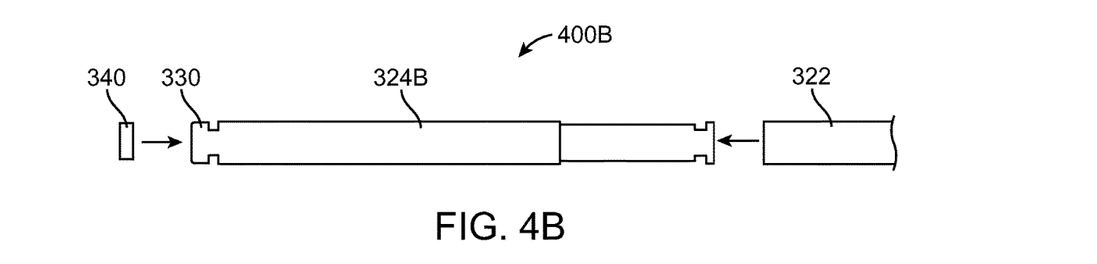
FIG. 4B illustrates a portion of a sheath in accordance with an embodiment of the invention in which the material in a section of a sheath covering a wrist mechanism differs from the material in an adjacent portion of the sheath.

FIG. 4B shows an exploded view of an alternative embodiment in which body 320 has separate pieces corresponding to sections 322 and 324B and is therefore easily made of different materials. For example, section 322 and a retaining structure 340 can be made of a relatively rigid material such as polyester, a multi-ply Mylar/Kapton or a rigid silicon or urethane, while section 324B is made of a more flexible material such as a more flexible silicone or urethane. The flexibility of the material in section 324B permits molding tip seal 330 as an integral part of section 324B. However, such flexible materials may be too soft and prone to kinking, so that all or a portion of section 324B can be reinforced, for example, with braided fiber or a coil spring that could be on the inside diameter, outside diameter, or within the material of section 324. The tubular sections 322 and 324B of different materials or different durometer of the same material are bonded or glued together to form body 320. FIG. 4B also illustrates that retaining structure 340, which is preferably made of a more rigid material, can be bonded to section 234B, so as to extend through a cutout in section 324B, enabling structure 340 to engage a complementary feature of an instrument to be sheathed, thereby locking sheath 400C in a desired location.

Figure 4C:
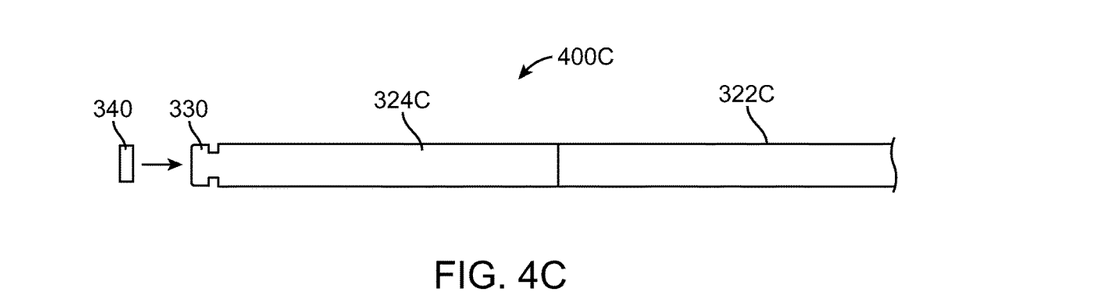
FIG. 4C illustrates a portion of a sheath in accordance with an embodiment of the invention that processes sections of the sheath differently to create different flexibility characteristics in different sections of the sheath.

FIG. 4C shows a portion 400C of yet another embodiment of a sheath having sections 322C and 324C made of the same initial material but may be processed to provide different characteristics. In particular, both sections 322C and 324C sheath 400C can made of a material such as silicon or expanded PTFE. However, section 322C may be processed or chemically treated to increase rigidity and improve abrasion resistance or section 324C may be treated or processed to improve performance during bending. The processing or treatment of a section may, for example, be a coating or dye that stiffens section 322C to facilitate installation of sheath 400C.

In an exemplary embodiment of sheath 400C, body 320 is made of PTFE that is processed at least in section 324C to make the PTFE porous. The density of PTFE in section 324C can thus be manipulated to provide the desired characteristics. For example, PTFE can be extruded and then stretched on an annealing mandrel to give the PTFE small tears or pores. The degree of porosity and the thickness of the PTFE material in section 324C can be selected to provide the required flexibility characteristics when the joint surrounded by section 324B bends. In particular, at a bending joint, one side of section 324B stretches or gets longer, while the other side contracts or gets shorter. The pores in section 324B open and close as the joint bends, so that section 324 can avoid changing in diameter and therefore does not get trapped or pinched by the bending joint. Expanded PTFE (or ePTFE) capable of bending in this manner is available commercially, for example, from International Polymer Engineering of Tempe, Ariz. Section 324 when made of ePTFE can have a silicone tip molded onto its ends to provide seals as described above or the ePTFE can provide a tension or friction seal when the ePTFE conforms to the underlying surface of the instrument. One advantage of PTFE is that it is very slick, which facilitates installation on an instrument and insertion of a sheathed instrument through a cannula. Colorant can be added to the PTFE if the bright white color of PTFE is distracting or causes saturation of the contrast of a camera system in a robotic medical system.

Figure 5:
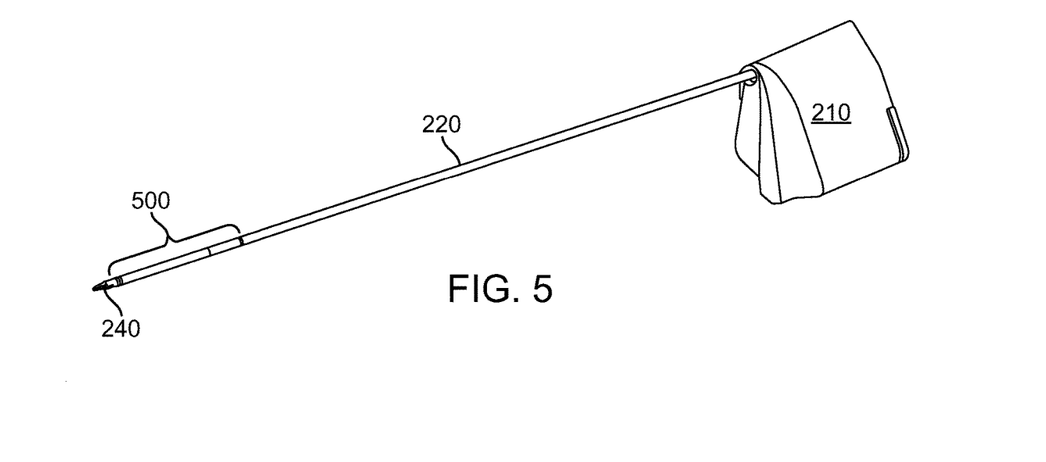
FIG. 5 illustrates an instrument in accordance with an embodiment of the invention in which a replaceable sheath covers a wrist mechanism of the instrument but does not extend the length of the main tube of the instrument.

Sheaths as described above can cover all or most of the length of main tube 220 and wrist mechanism 230 of an instrument 200 and particularly cover portions of the instrument that require electrical isolation, a barrier to biological material, or sealing to prevent loss of cavity pressure during a medical procedure. However, in an alternative embodiment of the invention, a replaceable sheath can be of more limited length and designed primarily to cover and seal a wrist mechanism or joint. FIG. 5, for example, shows an instrument having a replaceable sheath 500 that extends from effector 240 to the distal end of main tube 220, thereby covering and sealing the wrist mechanism of the instrument. The portion of main tube 220 not covered by sheath 500 can be left bare if sealing or electrical isolation of main tube 220 is not required or can be covered by a permanent coating or sheath that is not easily removable or replaceable.

A sheath covering a wrist mechanism, whether or not the remainder of the main tube of an instrument is covered, can be used to apply lubricants or agents to the wrist mechanism or other components of the instrument. For example, a medically safe lubricant such as mineral oil or Aesculap Sterilit oil can be coated on the interior of a sheath so as to come in contact with the wrist mechanism of an instrument when the removable sheath is installed on the instrument. In such a case, installation of the sheath and operation of the wrist mechanism can cause the lubricant to work into the wrist mechanism, resulting in less operating friction and less wear on mechanical joints. Alternatively or additionally, an agent that facilitates cleaning of an instrument can similarly be provided within the interior of the sheath. For example, an anticoagulant such as Heparin could be provided within a sheath so that biological material that somehow reaches the interior of the instrument is less likely to stick to the instrument and is more easily cleaned out of the instrument. Alternatively, the agent could be a disinfectant.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:
1. A surgical apparatus, comprising:
   a surgical instrument having a shaft, a joint, and an end effector coupled in series;
   one or more openings on the shaft, in the joint, or both on the shaft and in the joint, the one or more openings providing flow communication between an exterior of the shaft and an interior of the shaft;
   a sheath having a hollow body including a first portion and a second portion, the sheath being in an operable position on the surgical instrument so as to prevent infiltration of biological material through the one or more openings by the first portion covering the shaft and the second portion covering the joint on a condition that the one or more openings are on the shaft, the one or more openings are in the joint, or the one or more openings are on the shaft and in the joint;
   wherein the sheath is removably engaged with the shaft of the surgical instrument to retain the sheath in the operable position on the surgical instrument and to permit removal of the sheath from the surgical instrument; and
   wherein the second portion of the hollow body is made of flexible porous material, the flexible porous material having a pore structure providing a barrier to passage of liquids and enabling the second portion of the hollow body to substantially retain its cross-sectional shape or diameter when in a bent configuration, the flexible porous material comprising a colorant.

2. The surgical apparatus of claim 1, wherein the second portion of the hollow body has a non-corrugated outer surface profile.

3. The surgical apparatus of claim 1, wherein the porous material comprises expanded PTFE.

4. The surgical apparatus of claim 1, further comprising an end piece located at a distal end of the sheath, the end piece configured to form a seal with the surgical instrument and prevent biological material from entering between the sheath and the surgical instrument.

5. The surgical apparatus of claim 4, wherein the seal formed by the end piece is located at a distal tip portion of the sheath.

6. The surgical apparatus of claim 4, the surgical instrument further comprising a wrist that includes the joint, wherein the seal formed by the end piece is located distal to the wrist of the surgical instrument.

7. The surgical apparatus of claim 6, wherein the seal formed by the end piece seals the wrist of the surgical instrument in the operable position of the sheath on the surgical instrument.

8. The surgical apparatus of claim 1, wherein the first portion of the hollow body covers at least a portion of the shaft configured to be inserted within a body of a patient during a medical procedure.

9. The surgical apparatus of claim 1, wherein the first portion of the hollow body is bonded to the second portion of the hollow body.

10. The surgical apparatus of claim 1, wherein the surgical instrument further comprises a backend mechanism coupled at a proximal end of the shaft, the backend mechanism mechanically coupling drive tendons to at least one of the joint and the end effector.

11. The surgical apparatus of claim 10, further comprising a releasably locking retaining structure, the sheath being positioned on the surgical instrument such that the retaining structure is releasably locked to the surgical instrument proximate the backend mechanism.

12. The surgical apparatus of claim 11, wherein the retaining structure is shaped to engage a complementary feature on the shaft.

13. The surgical apparatus of claim 12, wherein one of the retaining structure and the complementary feature comprises one or more ridges, and the other of the retaining structure and the complementary feature comprises one or more grooves to receive the one or more ridges.

14. The surgical apparatus of claim 12, wherein the retaining structure comprises a resilient material.

15. The surgical apparatus of claim 12, further comprising an end piece attached to the first portion of the hollow body, wherein the end piece comprises the retaining structure.

16. The surgical apparatus of claim 15, wherein the end piece comprises a material differing from the first portion of the hollow body.

17. The surgical apparatus of claim 15, further comprising a second end piece attached to the second portion of the hollow body, the second end piece comprising a second retaining structure shaped to engage a second complementary feature of the surgical instrument.

18. The surgical apparatus of claim 17, wherein the second end piece is located at a distal end of the second portion of the hollow body.

19. The surgical apparatus of claim 1, wherein first portion of the hollow body exhibits higher rigidity than the flexible porous material of the second portion of the hollow body.

20. The surgical apparatus of claim 1, wherein the colorant is sufficient to reduce saturation of contrast when the flexible porous material of the sheath is imaged through an endoscopic camera.

* * * * *